United States Patent
Cohen et al.

(10) Patent No.: US 9,364,358 B2
(45) Date of Patent: Jun. 14, 2016

(54) CATHETER WITH RETRACTABLE COVER AND PRESSURIZED FLUID

(75) Inventors: Itshak Cohen, Ramat Hasharon (IL); Shahar Maximuk, Rishon LeZion (IL); Gilad Moiseyev, Givatayim (IL)

(73) Assignee: Medinol Ltd., Tel Aviv (IL)

( * ) Notice: Subject to any disclaimer, the term of this patent is extended or adjusted under 35 U.S.C. 154(b) by 812 days.

(21) Appl. No.: 13/560,132

(22) Filed: Jul. 27, 2012

(65) Prior Publication Data
US 2014/0031797 A1    Jan. 30, 2014

(51) Int. Cl.
A61F 2/966    (2013.01)
A61F 2/95    (2013.01)

(52) U.S. Cl.
CPC ......... A61F 2/966 (2013.01); *A61F 2002/9522* (2013.01); *A61F 2250/0003* (2013.01)

(58) Field of Classification Search
CPC ........... A61F 2/962; A61F 2/95; A61F 2/966; A61F 2002/9534; A61F 2002/9505; A61F 2002/9522; A61F 2250/0003; A61F 2/958; A61F 2002/011; A61F 2002/9517; A61M 25/0119
See application file for complete search history.

(56) References Cited

U.S. PATENT DOCUMENTS

| | | | |
|---|---|---|---|
| 4,732,152 A | 3/1988 | Wallstén et al. | |
| 5,571,135 A | 11/1996 | Fraser et al. | |
| 6,059,813 A | 5/2000 | Vrba et al. | |
| 6,238,410 B1 | 5/2001 | Vrba et al. | |
| 6,544,278 B1 | 4/2003 | Vrba et al. | |
| 6,942,682 B2 | 9/2005 | Vrba et al. | |
| 7,794,488 B2 | 9/2010 | Vrba et al. | |
| 8,066,754 B2 | 11/2011 | Malewicz | |
| 8,377,109 B2 | 2/2013 | Vrba et al. | |
| 8,845,712 B2 | 9/2014 | Irwin et al. | |
| 2005/0033402 A1* | 2/2005 | Cully et al. | 623/1.11 |
| 2006/0025844 A1 | 2/2006 | Majercak et al. | |
| 2006/0030923 A1* | 2/2006 | Gunderson | 623/1.11 |
| 2007/0208350 A1* | 9/2007 | Gunderson | A61F 2/95 606/108 |
| 2011/0118817 A1* | 5/2011 | Gunderson | A61F 2/95 623/1.12 |

FOREIGN PATENT DOCUMENTS

WO    WO 2013/025470    2/2013

OTHER PUBLICATIONS

Invitation and Partial International Search Annex from corresponding PCT Application No. PCT/2013/002770 dated Apr. 22, 2014, 5 pages.
International Search Report and Written Opinion from corresponding PCT Application No. PCT/2013/002770 dated Jun. 18, 2014, 18 pages.

* cited by examiner

*Primary Examiner* — Jocelin Tanner
(74) *Attorney, Agent, or Firm* — Cadwalader, Wickersham & Taft LLP

(57) ABSTRACT

Apparatus and method for delivering and deploying an intravascular device into the vessel including an outer and inner tube that are axially linked by a housing structure at the proximal end of the catheter, and a retractable sleeve structure having a middle tube and sleeve tip. The sleeve tip is sealed to the inner tube at the distal end, and continuously extends into the middle tube. At the proximal end of the sleeve structure, the middle tube is sealed to either a housing structure or slideable proximal ring, forming a sealed chamber between the inner tube and the sleeve structure. A radial space is formed between the sleeve tip and the inner tube optimized for intravascular device placement. During retraction of the sleeve structure, the fold of the sleeve tip peels away from the device, which expands to its deployed state while minimizing axial forces and friction.

39 Claims, 8 Drawing Sheets

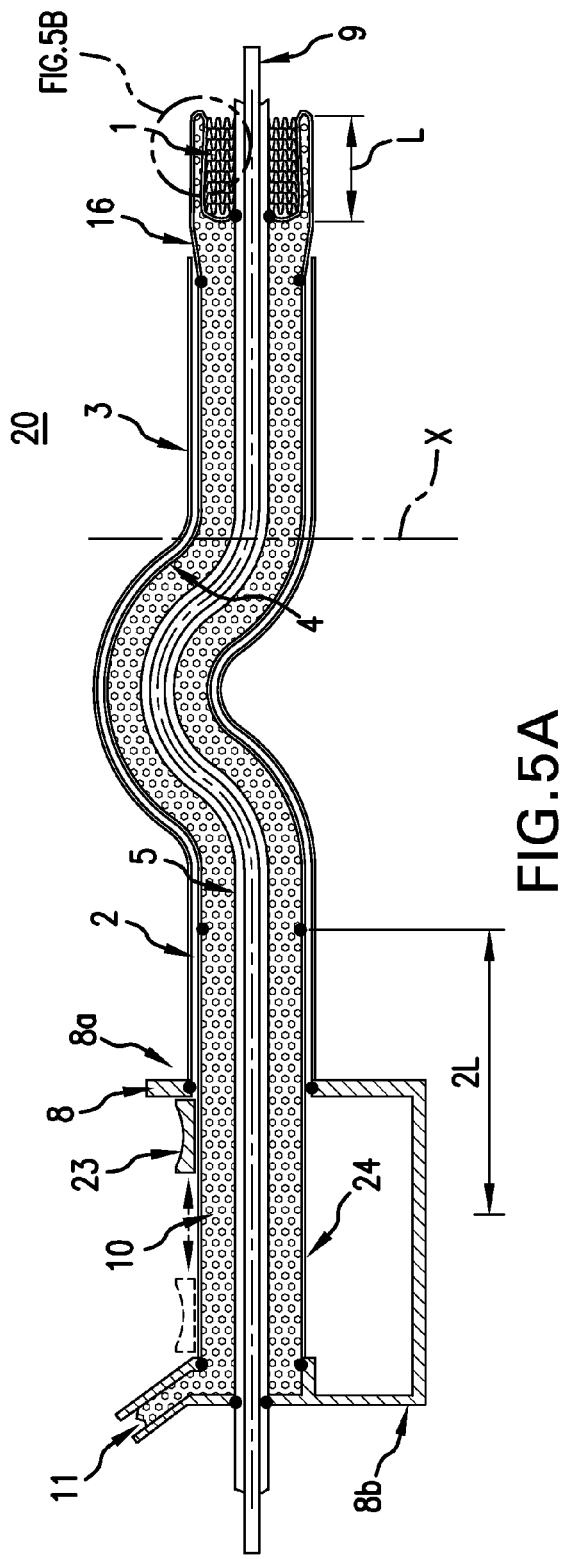
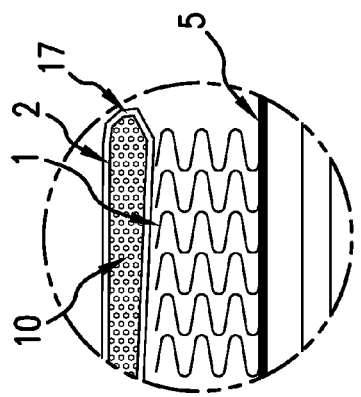
FIG.5A
FIG.5B

CATHETER WITH RETRACTABLE COVER AND PRESSURIZED FLUID

FIELD OF THE INVENTION

The present invention relates to the field of catheters, in particular a catheter system with a retractable sleeve structure for use, for example, in delivery and deployment of an intravascular device. The catheter system is specifically designed for use in the delivery of an intravascular device through tortuous vessels and its deployment therein.

BACKGROUND

Transluminally implantable intravascular devices, such as stents or grafts, are initially mounted upon or within a delivery catheter and then crimped into a compact configuration of a relatively small diameter to facilitate insertion and transluminal advancement of the device into the desired lesion requiring treatment. Thereafter, such devices are radially expanded to a larger operative diameter either by removing a constraining layer thereby releasing the device or by inflating a balloon on which the device is crimped. When expanded the device serves to support the vessel against its tendency to reclose and may also serve as a matrix for releasing a medically active substance.

It will be appreciated that the term "stent" may be used herein below as a general and non-limiting example of a catheter-mounted intravascular device. Both self-expanding and balloon expandable stents are well known and widely available in a variety of designs and configurations.

Prior art catheter systems for stent delivery provided a restraining sheath as a retractable sheath overlying the stent. One problem that arises when mounting the stent on the catheter system as well as during retraction of the sheath is excessive friction and rubbing between the sheath and the stent that may complicate and sometimes render stent deployment impossible. In addition, stents are often coated with a special polymer, a drug, or a combination thereof. Excessive friction and rubbing between the stent and the constraining sheath may cause damage to the integrity of the coated surface material of the stent by the friction between the sheath and the external surface of the stent. Moreover, such friction tends to increase even more when using longer stents or stents with a narrower crimping profile. Accordingly, it is an object of the invention to minimize friction between the catheter and the stent during deployment.

Another problem in the art arises with stents having relatively low axial rigidity, where axial friction forces applied during deployment or mounting of the stent on the catheter system may shorten the stent. It is therefore advantageous to have a catheter system that minimizes axial friction forces applied to the stent during deployment and mounting.

Yet another problem known in the art is related to the size of the proximal portion or the handle of catheter systems of self-expandable stents. Deploying such stents requires pulling the constraining sheath backward in the proximal direction a length which equals at least the length of the stent. When using longer stents (i.e. 100 millimeters and more) this limitation becomes a disadvantage as it leads to relatively long handles with a bulky mechanical structure that may be uncomfortable to operate. It is therefore advantageous to have a catheter system with a relatively short handle.

SUMMARY OF THE INVENTION

The present invention relates to a catheter system with a retractable sleeve structure and a method of using the catheter system. The catheter system comprises a multi-component tubular structure capable of deploying an intravascular device while minimizing axial frictional loads on the device during deployment. The catheter system of the invention uses a retractable sleeve structure filled with fluid during delivery and deployment. For the purpose of this application, "fluid" is understood according to its proper definition in the area of physics and therefore includes without limitations, substances in a gaseous phase as well as substances in a liquid phase. The catheter system comprises an inner tube disposed coaxially with an outer tube, wherein the inner tube comprises an interior lumen for a guide wire and an exterior surface on which a retractable sleeve structure is mounted. The outer tube forms a lumen for each of the guide wire, inner tube and the retractable sleeve structure.

The retractable sleeve structure extends through the length of the inner tube and forms a sealed chamber therewith. The retractable sleeve structure comprises a middle tube and a distal sleeve tip, the sleeve tip forming a fold over the distal end of the intravascular device thereby creating a double layered sheath around the device. The double layered sheath, when pressurized with fluid, may be pulled back and release the device without exerting any friction forces thereon.

The invention also relates to a method of deploying an intravascular device. The method comprises the steps of filling the sealed chamber with fluid, navigating the catheter to a target site, positioning the sleeve tip with a mounted device at the target site, pressurizing the fluid and pulling the retractable sleeve structure proximally, thereby causing the sleeve tip to unfold and release the device at the target site without exerting any friction forces on the device. In one embodiment the retractable sleeve structure is pulled back by sliding a handle connected to a proximal portion of the middle tube. In another embodiment the retractable sleeve structure is pulled back by applying a force to a collapsible proximal portion of the middle tube using, for example, a knob or wheel. The force in the proximal direction may push the collapsible proximal portion towards the proximal end of the housing structure, thereby collapsing the collapsible portion, for example, in an accordion-like fashion. This embodiment has an advantage in that it enables the use of a shorter guide wire and shorter housing compared to other catheter systems, and is particularly useful when using relatively long stents.

Another aspect of the invention relates to a method of mounting an intravascular device onto the catheter system. In one embodiment the method comprises the steps of retracting the sleeve tip to an unfolded position, filling the retractable sleeve structure with fluid, and holding a crimped intravascular device onto the inner tube with a separate device, and advancing the sleeve tip over the crimped intravascular device thereby forming a fold over a portion of the crimped intravascular device. In this mounting embodiment, the intravascular device is released, the catheter system is pulled proximally, and the process is incrementally repeated until the intravascular device is mostly or entirely located under the fold of the sleeve tip. Once the intravascular device is fully sheathed by the fold, the method may further comprise releasing the fluid within the sealed chamber for storage. This aspect of the invention may be useful in particular to mount an intravascular device onto a catheter system for later deployment according to the method of deploying an intravascular device indicated above.

Storage of the catheter system may be accomplished at a neutral air pressure. However, prior to use, the air in the retractable sleeve structure is replaced with fluid through the use of a sealable port. During this process, any residual air in the sleeve structure escapes through a micro-orifice in the fold of the sleeve tip.

DESCRIPTION OF DRAWINGS

FIG. 5A illustrates one alternative embodiment of the catheter system according to the principles of the present invention.

FIG. 5B illustrates an enlarged portion of FIG. 5A.

Figure 1A:
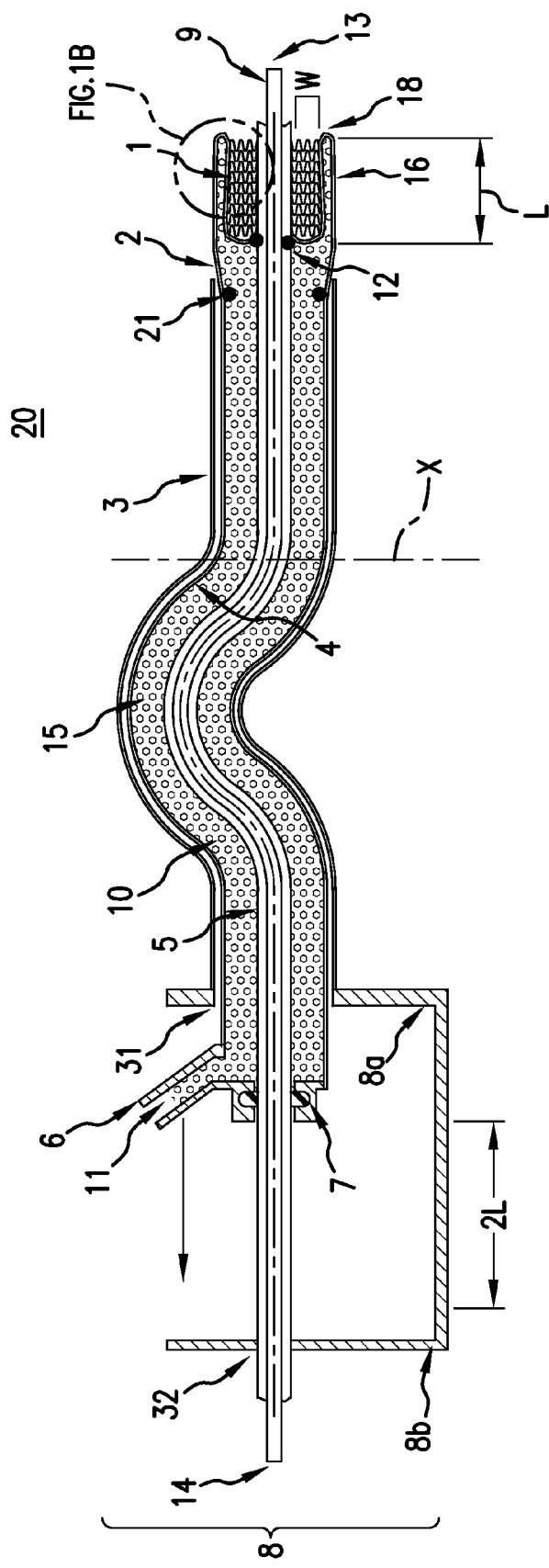
FIG. 1A illustrates the catheter system in a pre-deployment state according to the principles of the invention.

The intravascular devices shown in these Figures are two-dimensional representations of the intravascular device embodiments of the instant invention. The skilled artisan will recognize that the device is a three-dimensional structure having a cylindrical portion, as described further below.

DETAILED DESCRIPTION OF THE INVENTION

The catheter system with a retractable sleeve structure of the invention allows an intravascular device to be delivered to a target vessel without subjecting the device to frictional forces during deployment associated with other delivery systems using a constraining sheath. The catheter system of the invention includes an elongate inner tube defining proximal and distal ends and a lumen extending longitudinally therethrough wherein a guide wire is movably disposed. The catheter system further includes an elongate outer tube having a proximal and a distal end, wherein the inner tube coaxially extends therethrough along the entire length. The inner tube and outer tube are affixed to a housing structure in the proximal portion of the catheter system, the housing structure includes a distal opening to which the outer tube is affixed, as well as a proximal opening to which the inner tube is affixed. "Distal" is defined herein as being closer to the insertion end of the catheter (i.e. the end typically inserted into the body) and the term "proximal" is defined as being closer to the end of the catheter that generally remains outside the body, as demarcated by line X in the Figures herein.

A retractable sleeve structure having a proximal and a distal end extends through the axial space created between the inner and the outer tubes. The retractable sleeve structure comprises a middle tube and a sleeve tip which coaxially extends substantially along the length of the inner and outer tubes. The retractable sleeve structure may be sealingly connected to the inner tube at the distal end with a distal ring thereby forming a sealed chamber. In a pre-deployment state the intravascular device is mounted in a radial space created between the inner tube and a doubled layered sheath created by folding the sleeve tip onto itself.

In one embodiment, a proximal ring sealingly connects the retractable sleeve structure to the inner tube within the housing. The proximal end of the retractable sleeve structure may further comprise a handle designed to facilitate moving the retractable sleeve structure from a distal position within the housing structure to a proximal position. The retractable sleeve structure further comprises a sealable port. The retractable sleeve structure together with the inner tube form a sealed chamber, in which fluid may be added or removed through the sealable port. The retractable sleeve structure may be retracted by sliding the handle from a first distal position to a second more proximal position, thereby withdrawing and unfolding the sleeve tip and releasing the device. Because the outer tube and the inner tube are fixedly connected to the housing structure, the outer and inner tubes are not affected by sliding the handle of the retractable sleeve structure.

Referring now to the drawings wherein the showings are for purposes of illustrating preferred embodiments of the present invention only, and not for purposes of limiting the scope of the invention in any way, FIG. 1A shows one embodiment of the catheter system 20 in a pre-deployment state having a proximal end and a distal end. The catheter system includes a guide wire 9 comprising a distal end 13 extending into the lumen during deployment and a proximal end 14 that remains outside the body during deployment. The guide wire 9 extends through the lumen of inner tube 5. The inner tube 5 has a proximal end and a distal end. The inner tube 5 extends through housing structure 8 having a distal end 8a and a proximal end 8b. In this embodiment, the housing structure 8 has a length equal to or greater than a distance 2L, i.e. a length twice distance L (detailed herein below). The housing structure 8 includes a distal opening 31 and a proximal opening 32. The inner tube 5 extends through distal opening 31 of the housing structure 8 to the proximal opening 32, to which the inner tube 5 is affixed. In FIG. 1A, the inner tube 5 traverses the proximal opening 32 through the housing structure 8. Outer tube 3 forms a lumen through which extends the inner tube 5 and guide wire 9. The outer tube 3 is affixed to the housing structure 8 at distal opening 31.

The outer tube 3, the middle tube 4 and inner tube 5 may be manufactured from kink resistant and flexible materials or composite structures, for example polyether ether ketone (PEEK), polyethylene terephthalate (PET), Polyimide (PI), braided Nylon 12 or suitable materials readily understood in the art. The method of affixing the outer tube 3 and inner tube 5 to the housing structure 8 can be achieved through methods that are well known in the art. Non-limiting examples of joining methods include fusing (e.g. heat fusion), welding (e.g. ultrasonic welding) and joining by adhesive methods (e.g., gluing). Combinations of these methods are contemplated by this invention.

The outer tube 3 and the inner tube 5 are affixed to the housing structure 8, and form a consistent radial space between the outer surface of the inner tube 5 and the internal surface of the outer tube 3. A retractable sleeve structure 2 extends through the radial space formed by outer tube 3 and inner tube 5. The retractable sleeve structure 2 comprises middle tube 4 having a proximal end and a distal end and a sleeve tip 16 having a proximal end and a distal end. In one embodiment, as shown in FIG. 1A, the proximal end of middle tube 4 is sealingly connected to the inner tube 5 via proximal ring 7. In the embodiment of FIG. 1A, the proximal ring 7 forms a fluid-tight, moveable seal against inner tube 5.

The retractable sleeve structure 2 further comprises a handle 6 which may be utilized to control movement of the retractable sleeve structure 2, including movement of the slideable proximal ring 7 along inner tube 5. In FIG. 1A, the handle 6 further comprises a sealable port 11 for controlling the contents and pressure of sealed chamber 15 formed by the retractable sleeve structure 2 together with the inner tube 5. In another embodiment, the sealable port 11 may be positioned on the middle tube 4 separate from the handle 6. The distal end of middle tube 4 is fixed to the proximal end of the sleeve tip 16. The distal end of the sleeve tip 16 may be sealed to the inner tube 5 via a distal ring 12 as shown in FIG. 1A. Pressurized fluid 10 may be introduced into the sealed chamber 15 formed by the retractable sleeve structure 2 and inner tube 5 through the sealable port 11. Similarly, the pressure of the fluid in the retractable sleeve structure may be controlled via the sealable port 11. Generally, the housing structure of any embodiment described herein may be an open or closed structure.

Figure 1B:
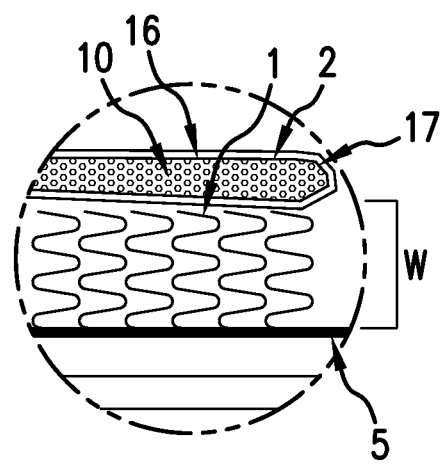
FIG. 1B illustrates an enlarged portion of FIG. 1A.

In one embodiment, the retractable sleeve structure has, while pressurized, a substantially constant outer diameter along the longitudinal extent of the middle tube 4 and sleeve tip 16. The sleeve tip 16 radially extends a radial distance W from inner tube 5 and folds onto itself forming a sheath around the crimped device 1. While the device may be any transluminally implantable intravascular device, the device 1 depicted in FIG. 1A and other Figures is a cylindrical stent, here illustrated in a crimped state. Fold 17 of the retractable sleeve structure 2 extends a longitudinal distance L which is equal to or greater than the length of the intravascular device. FIG. 1B shows an enlarged portion of the catheter system 20, including the fold 17 of the sleeve tip 16 that forms a radial distance W between the retractable sleeve structure 2 and the inner tube 5. The space formed between the sleeve tip 16 and inner tube 5 is suitable for mounting a device 1 prior to deployment. In this embodiment the fold length L closely matches the length of the mounted device 1.

The invention also relates to a method of deploying an intravascular device. The first deployment step comprises pressurizing the retractable sleeve structure 2 with fluid. In one embodiment, the retractable sleeve structure 2 is packaged at neutral air pressure such that the operator will pressurize the retractable sleeve structure 2 with fluid prior to its use. During pressurization of the retractable sleeve structure 2 with fluid, it may be necessary to remove remaining air from the sleeve. A micro-orifice 18 in the sleeve tip 16 allows any remaining air to evacuate the sealed chamber 15 prior to or while the sealed chamber 15 is filled with a pressurized fluid 10 by applying a force of 1-2 atm through the sealable port 11. The micro-orifice 18 preferably has a diameter in the range of 30-40 micrometers, thus allowing air to exit the sealed chamber 15 while generally preventing pressurized fluid from exiting. Insertion and pressurization of the fluid 10 can be achieved using methods that are well known in the art. In one embodiment, physiologically-compatible fluid is used in the sealed chamber, such as, for example, a physiologically-compatible saline solution. Other biocompatible fluids may similarly be used as is known in the art. The sealed chamber 15 may be filled to a pressure in the range of 1-10 Atm. In one preferred embodiment, the sealed chamber 15 is pressurized to 4 Atm.

Employment of a pressurized fluid may provide an advantage by maintaining the adjacent inner and outer portions of the fold of the sleeve tip apart from each other by at least a few micrometers so as to avoid rubbing. The method of evacuating air through a micro-orifice in the distal portion of the sleeve tip is advantageous compared to other methods known in the art for evacuating air (e.g. by application of a vacuum) because the micro-orifice enables evacuation of a greater percentage of residual air from the sealed chamber.

The method of deploying an intravascular device further comprises navigating the sleeve tip to the target site in the body lumen so that the mounted device 1 is positioned at the target site for deployment. The sleeve tip is delivered to the target site in the body lumen by methods known in the art. The employment of thin, flexible, light-weight materials, as well as the use of pressurized fluid in the retractable sleeve structure, enables the catheter system 20 to navigate a tortuous lumen while minimizing axial and frictional forces on the body lumen.

Figure 2:
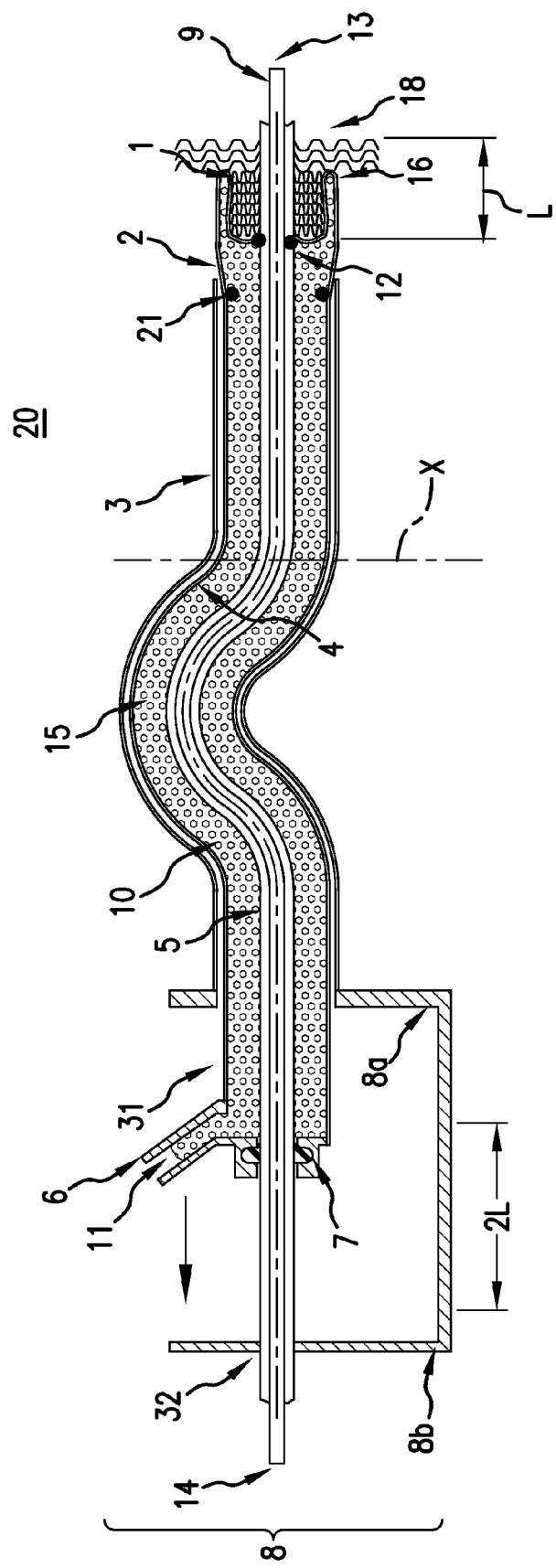
FIG. 2 illustrates the catheter system in a stage of partial deployment of an intravascular device as the sleeve tip of the retractable sleeve structure is partially withdrawn by sliding the handle one-third of the distance toward the proximal end of the housing structure.
Figure 3:
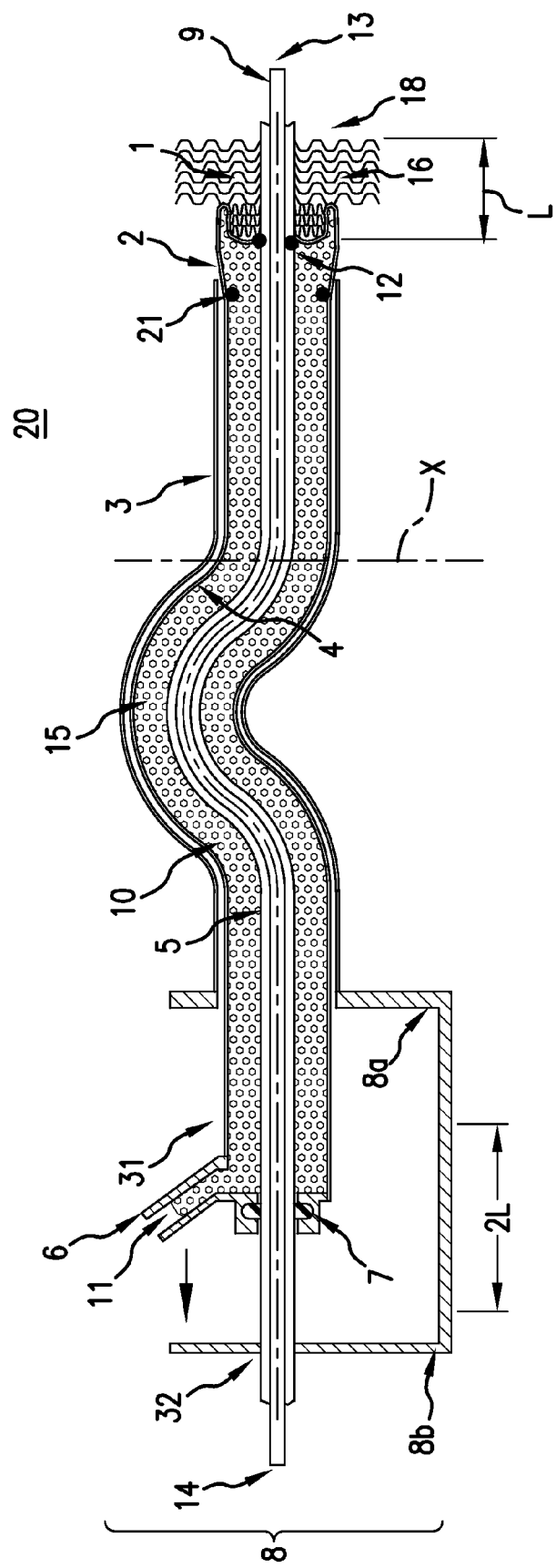
FIG. 3 illustrates the catheter system in a stage of partial deployment of an intravascular device as the sleeve tip of the retractable sleeve structure is partially withdrawn by sliding the handle two thirds of the distance toward the proximal end of the housing structure.
Figure 4:
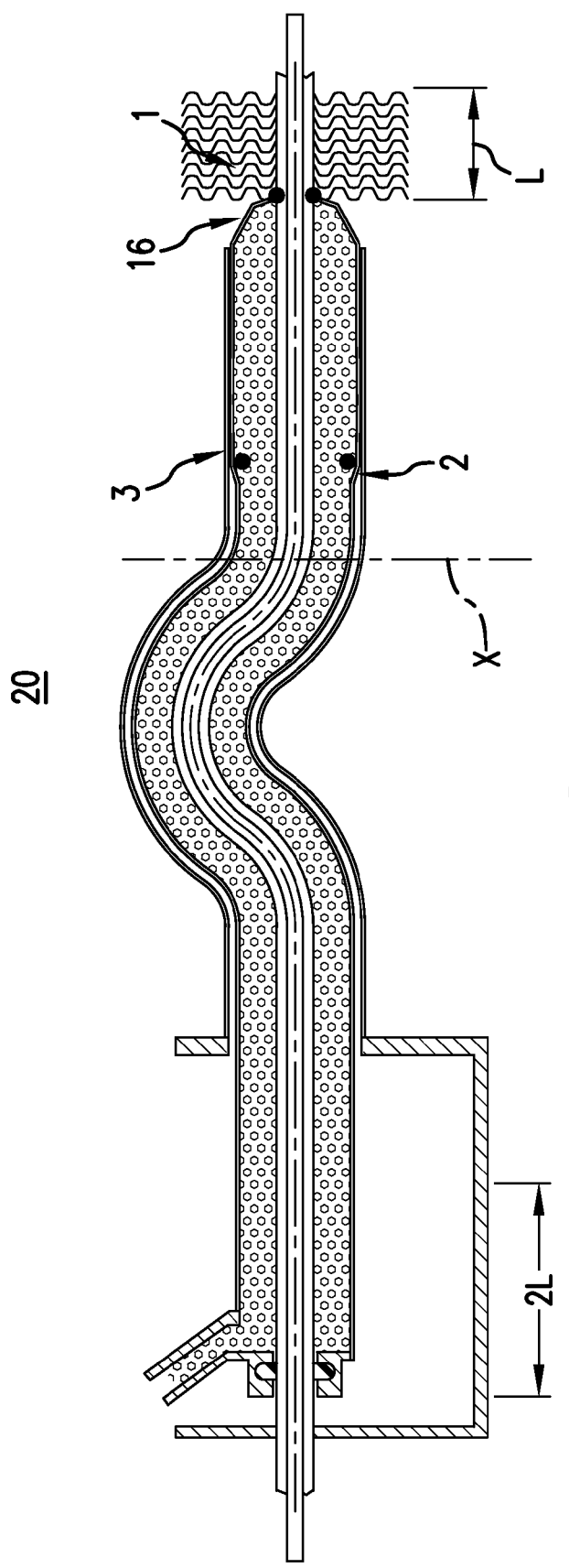
FIG. 4 illustrates the catheter system in a post-deployment state according to the principles of the invention.

The method of deploying an intravascular device further comprises retracting the retractable sleeve structure 2, whereby the sleeve tip 16 is withdrawn or peeled away from the device in a proximal direction, thereby releasing the device 1. FIGS. 1 through 4 illustrate this step according to one embodiment of the invention. With reference to FIG. 1, the handle 6 of the retractable sleeve structure 2 begins in a first position near the distal end of the housing structure 8. In one embodiment of this invention, the retraction step comprises applying a proximally-directed force on the handle 6, thereby sliding the proximal ring 7 in a longitudinal direction along the inner tube 5. As shown in FIG. 2, as the proximal ring 7 slides a distance of approximately one-third of 2L, the sleeve tip 16 withdraws a longitudinal distance of approximately one-third of L. Because the outer tube 3 and inner tube 5 are fixedly connected to the housing structure 8—which remains stationary during this step—only the retractable sleeve structure is affected by applying a proximally-directed force to the handle 6 and sliding the handle 6 in a proximal direction. This step is further illustrated by FIG. 3, wherein the handle 6 and proximal ring 7 slides a distance of approximately two-thirds of 2L, and the sleeve tip 16 therefore withdraws a longitudinal distance of approximately two-thirds of L. The step is completed, as shown in FIG. 4 with the full deployment of the device 1 by sliding the proximal ring 7 and handle 6 the entire distance 2L to a second position adjacent to the proximal end 8b of the housing structure 8, thereby withdrawing the sleeve tip 16 a distance L. The retraction of the retractable sleeve structure 2 thereby releases the device 1 while minimizing friction on the exterior surface of the device 1. The device 1 is then able to expand into the target site of the body lumen. Throughout the process, the proximal ring 7 maintains a liquid-tight seal against inner tube 5, thus maintaining pressurization of the retractable sleeve structure 2.

FIG. 4 shows the catheter system 20 in a post-deployment state. The retraction of the retractable sleeve structure 2 released the device 1 within the body lumen. As the retractable sleeve structure 2 is retracted, the fold 17 is peeled away from the intravascular device thereby releasing it into the body lumen. Retraction of the sleeve structure a distance of 2L will result in withdrawal of the sleeve tip fold 17 a length L.

Figure 6:
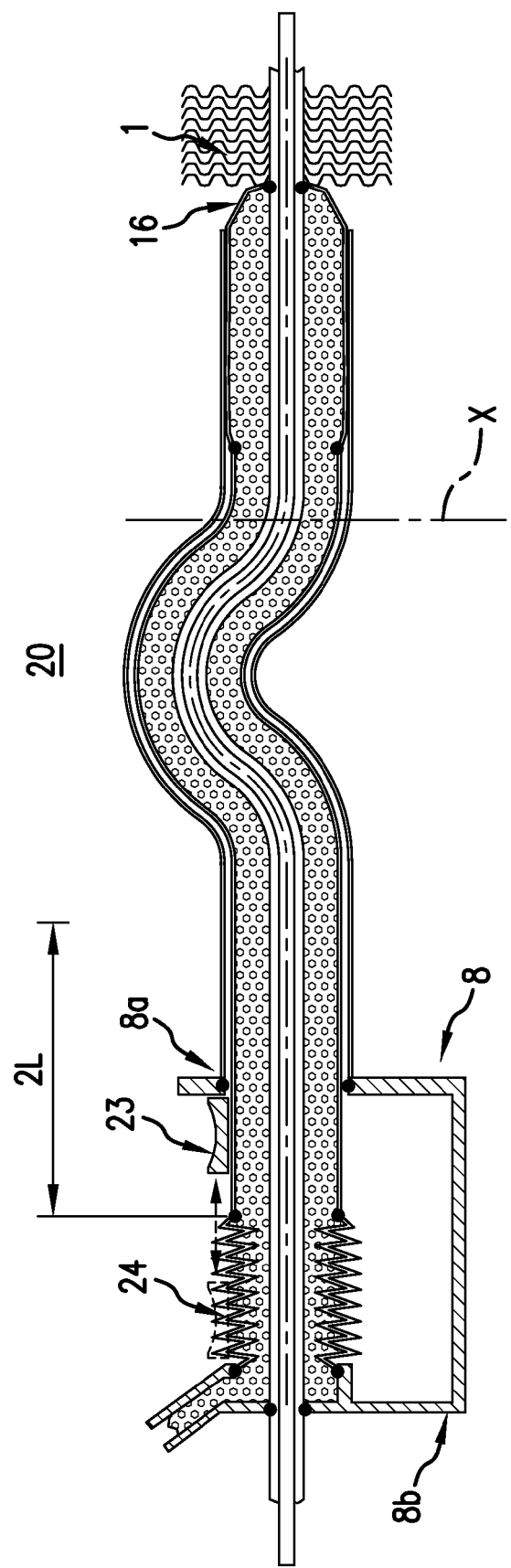
FIG. 6 illustrates another alternative embodiment of the catheter system according to the principles of the present invention.

FIG. 5A shows another embodiment of the catheter system 20, wherein the retractable sleeve structure 2 further comprises a collapsible proximal portion sleeve 24 sealingly attached at its proximal end to the proximal end 8b of the housing structure 8, and sealingly attached at its distal end to the middle tube 4. The collapsible proximal portion sleeve 24 is manufactured of a highly flexible material, such as, for example ultra-thin polyethylene terephthalate (PET) or a Polyimide (PI). In this embodiment, the proximal end of the retractable sleeve structure 2 is integral with the proximal portion of the housing structure 8. In FIG. 5A, the retractable sleeve structure 2 further includes a handle 23 which in this embodiment is formed as a knob positioned at the distal portion within the housing structure 8. During deployment, a radial force is applied to the handle 23, thereby axially compressing the retractable sleeve structure 2; simultaneously, a force in the proximal direction is applied to the handle 23, thereby collapsing the proximal portion sleeve 24, for example, into accordion-like folds as shown in FIG. 6. In other embodiments, the proximal portion sleeve 24 may collapse in other manners as known in the art. Because the embodiments illustrated in FIGS. 5A and 6 are based on collapsible proximal portion sleeve 24, these embodiments have the advantage of not requiring housing structures equal to or longer than twice the length of the stent (i.e. the length of the housing can be shorter than 2L), thereby making the catheter system more compact and easier to use.

FIG. 5B shows an enlarged portion of the catheter system 20, including the fold 17 of the sleeve tip 16. The sleeve tip is manufactured from materials having sufficient radial rigidity to prevent expansion beyond a desired maximum diameter. Non-limiting examples include ultra-thin polyethylene terephthalate (PET) or a Polyimide (PI). Advantages of a sleeve tip formed by PET include flexibility and kink resistance. In one embodiment, the sleeve tip is formed of a material about 5-20 micrometers thick, preferably 10 micrometers thick. The two adjacent portions of the sleeve tip created by the fold, i.e. the inner and outer portions of the fold, and extending a longitudinal distance 2L are maintained apart from each other preferably by a few micrometers so as to avoid rubbing against each other; such separation is enabled by pressurizing sealed chamber 15. The method of combining or joining the components of the retractable sleeve structure 2 can be achieved through methods that are well known in the art. Non-limiting examples of joining methods include fusing (e.g. heat fusion), welding (e.g. ultrasonic welding) and joining by adhesive methods (e.g., gluing). Combinations of these methods are contemplated by this invention. In one embodiment, for example, the distal end of the middle tube 4 is joined to the proximal end of the sleeve tip 16 by a middle connection ring 21 that provides adhesion.

The method of deploying the intravascular device of FIGS. 5 and 6 is accomplished by retracting the retractable sleeve structure 2 through a series of steps involving a handle 23, as shown in FIGS. 5A and 6. The retraction begins, as shown in FIG. 5A, with the handle 23 in a first position near the distal end 8a of the housing structure 8 along the collapsible proximal portion sleeve 24 of the retractable sleeve structure 2. The first step comprises applying a compression force to the handle 23, thereby gripping the handle 23 against the proximal portion sleeve 24. As illustrated by FIG. 6, the next step comprises pulling the handle 23 in a proximal direction while maintaining a compression force, thereby collapsing the collapsible proximal portion sleeve 24 toward the proximal end 8b of the housing structure 8 and releasing the intravascular device. In one embodiment, the collapsible proximal portion sleeve 24 folds in an accordion-like manner, as shown in FIG. 6. The method further comprises reducing the compression force on the handle 23 and returning the handle 23 to the first position near the distal end 8a of the housing structure 8. These steps are repeated until the collapsible proximal portion sleeve 24 of the retractable sleeve structure 2 has fully collapsed, thereby withdrawing the sleeve tip 16 and releasing the device 1, viewed either through an imaging medium (e.g. angiography) or as indicated by an abrupt increase in resistance to the retraction force on the handle 23. In another embodiment of the invention, employment of a wheel in this step may be used to apply a force to the proximal portion sleeve 24 in the proximal direction.

Figure 7A:
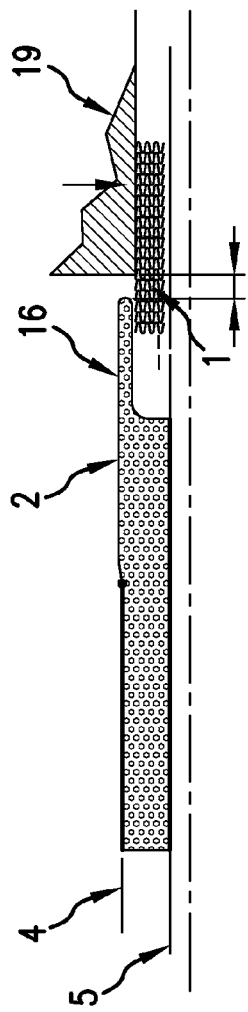
FIGS. 7A-7D illustrate a method of placing the intravascular device onto the catheter system and under the constraining sheath.
Figure 7B:
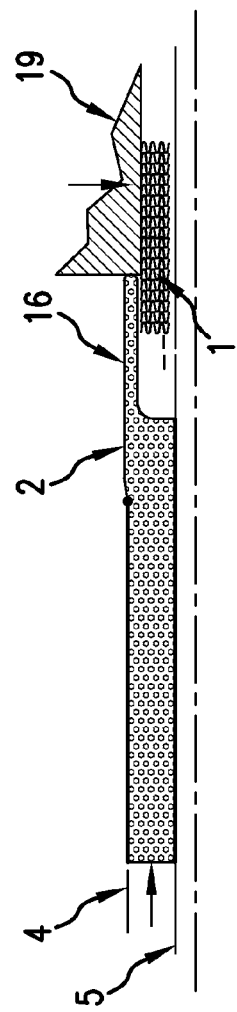
Figure 7C:
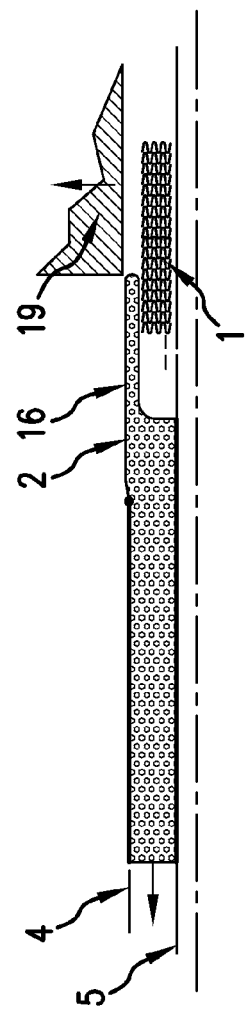
Figure 7D:
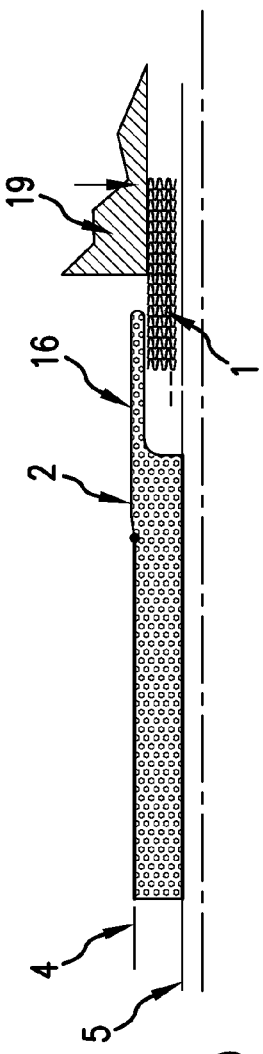

Many different methods may be employed to mount the intravascular device onto the inner tube of the catheter system prior to deployment. One method is illustrated by FIGS. 7A-7D. The first step of one embodiment is shown in FIG. 7A and comprises compressing at least a portion of intravascular device 1, for example a fully crimped stent, around an inner tube 5 using a holding device 19. The next step, shown in FIG. 7B, comprises applying a force in the distal direction, for example to the handle of the sleeve tip (not shown), such that the retractable sleeve structure moves in the distal direction to incrementally extend longitudinally over an exposed residual portion of the intravascular device. The axial rigidity of the sleeve tip 16 is accomplished by fluid pressurization through means discussed above. The method also comprises releasing the holding device 19 and pulling the catheter system proximally, as shown in FIG. 7C. In the next step, the process repeats, as shown in FIG. 7D. The holding device 19 is compressed against a more distal location on the device 1 than in the previous step and at each cycle the fold of the sleeve tip is extended incrementally in the distal direction to eventually cover or sheath the entire device. In one embodiment, the retractable sleeve structure 2 may be assembled with pressurized fluid in the sealed chamber 15. The sealed chamber may be deflated once the device is mounted and prior to use.

In another embodiment of the intravascular device mounting method, the method comprises placing a intravascular device in a crimped state on the inner tube while the handle of the retractable sleeve structure is positioned near the proximal end of the housing structure, such that the sleeve tip is fully withdrawn. In the next step of this embodiment, a force in the distal direction is applied to the handle, such that the retractable sleeve structure moves distally against the mounted intravascular device. Upon contact with the mounted intravascular device, the sleeve tip naturally folds around the intravascular device. A holding device is positioned at the distal end of the intravascular device holding it in place as the sleeve tip folds over the device. The fold of the sleeve tip is extended to cover or sheath the entire intravascular device.

The device may be any stent or graft device, which are well known in the art. Any stent design may be utilized in connection with the present invention. In one example, the stent consists of separate segments designed to expand independently from each other as the sleeve tip is withdrawn; however, it should be understood that the invention is not limited to any particular stent design or structure. A stent or graft having either separate segments or a unitary design (i.e., without separate stent segments designed to expand independently from each other) may be used with this invention, as well as stents that expand at different rates along the longitudinal axis of the stent. The invention further contemplates stents or grafts having diameters of variable sizes and different lengths. One non-limiting example design is the NIRflex stent which is manufactured by Medinol, Ltd., as described in U.S. Pat. No. 6,723,119, which is incorporated herein in toto, by reference. Another example of a suitable self-expanding stent is described in U.S. Pat. Nos. 6,503,270 and 6,355,059, for example, which are also incorporated herein in toto, by reference.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

The invention claimed is:

1. A catheter system having a distal end and a proximal end, the catheter system comprising:
   an inner tube having a first lumen;
   an outer tube having a second lumen, wherein said inner tube extends through said second lumen;
   a retractable sleeve structure positioned between the inner tube and outer tube, said retractable sleeve structure comprising a middle tube and a sleeve tip, said sleeve tip having a first configuration wherein an intravascular device is fully enveloped by said sleeve tip in said first configuration and a second configuration after deployment of said intravascular device, wherein said sleeve tip has an axial length in said first configuration and two times said axial length in said second configuration; and
   a housing structure at the proximal end of said catheter system, said housing structure having a distal end comprising a distal opening and a proximal end comprising a proximal opening, wherein said inner tube is affixed to the proximal opening of said housing structure;
   wherein said retractable sleeve structure and said inner tube form a sealed chamber.

2. The catheter system of claim 1 further comprising a distal ring connecting the sleeve tip to the inner tube.

3. The catheter system according to any of claim 1 or 2 further comprising a proximal ring connecting the middle tube to the inner tube.

4. The catheter system according to claim 1, wherein the sealed chamber contains a fluid.

5. The catheter system according to claim 1, wherein said sleeve tip forms a fold.

6. The catheter system of claim 5, having a radial space between the sleeve tip and the inner tube.

7. The catheter system according to claim 1, wherein said outer tube is affixed to the distal opening of said housing structure.

8. The catheter system according to claim 1, wherein the outer tube and inner tube are affixed relative to each other.

9. The catheter system according to claim 1, wherein the retractable sleeve structure is movable relative to the inner and outer tubes.

10. The catheter system of claim 1, further comprising a handle connected to the retractable sleeve structure.

11. A method of mounting an intraluminal intravascular device onto the catheter system of claim 10 comprising the following steps:
   (a) positioning the handle in a proximal position within the housing;
   (b) filling the sealed chamber with fluid;
   (c) holding the intravascular device onto the inner tube with a holding device; and
   (d) advancing the retractable sleeve structure distally to extend longitudinally over the device.

12. The method of claim 11 further comprising releasing the fluid from the retractable sleeve structure.

13. The catheter system according to claim 1, wherein the catheter system further comprises an intravascular device.

14. The catheter system according to claim 1, wherein said retractable sleeve structure comprises a sealable port.

15. The catheter system according to claim 1, wherein the sleeve tip includes a micro-orifice having a diameter of 30-40 micrometers.

16. The catheter system according to claim 1, wherein the middle tube comprises a kink resistant and flexible material.

17. The catheter system according to claim 1, wherein the outer tube comprises a kink resistant and flexible material.

18. The catheter system according to claim 1, wherein the inner tube comprises a kink resistant and flexible material.

19. The catheter system according to claim 1, wherein the retractable sleeve structure comprises ultra-thin polyethylene terephthalate.

20. The catheter system according to claim 1, wherein the retractable sleeve structure comprises polyimide.

21. The catheter system according to claim 1, wherein the retractable sleeve structure comprises a handle for moving the middle tube relative to the inner and outer tubes.

22. The catheter system according to claim 1, wherein the retractable sleeve structure comprises a collapsible proximal portion.

23. The catheter system of claim 22, wherein the retractable sleeve structure further comprises a handle connected to the collapsible portion, the handle adapted to axially compress the collapsible proximal portion.

24. A method of deploying an intravascular device from the catheter system of claim 1; comprising the steps of:
   (a) navigating said sleeve tip to a target site within a body lumen;
   (b) pressurizing fluid into said sealed chamber;
   (c) retracting the retractable sleeve structure to withdraw the sleeve tip; and
   (d) releasing the device.

25. The method of claim 24, further comprising: withdrawing the sleeve tip by applying a force to a handle connected to the retractable sleeve structure.

26. The method according to claim 24, further comprising: withdrawing the sleeve tip by applying a force to a collapsible proximal portion of the retractable sleeve structure.

27. The method according to claim 24, wherein said step of withdrawing the sleeve tip further unfolds a fold formed by said sleeve tip.

28. The method according to claim 24, further comprising pressurizing fluid to the sealed chamber through a sealable port.

29. The method according to claim 24, further comprising evacuating fluid from the sealed chamber through a micro-orifice.

30. The method according to claim 24, further comprising retracting the retractable sleeve structure a longitudinal distance longer than the length of the intravascular device.

31. The method according to claim 24, wherein said step of retracting the retractable sleeve structure does not apply any axial force on the device.

32. A method of mounting an intravascular device onto the catheter system of claim 1; comprising the following steps:
   (a) pressurizing the sealed chamber with fluid;
   (b) compressing at least a portion of said device around said inner tube; and
   (c) advancing said retractable sleeve structure so that the sleeve tip extends longitudinally over at least a part of an uncompressed portion of said device.

33. The method of claim 32 wherein said device is enveloped by a fold of said sleeve tip.

34. The method according to claim 32, further comprising an initial step of fully crimping said device onto the inner tube.

35. The method according to claim 32, wherein said step of advancing is done by applying a force in a distal direction to a handle connected to the sleeve structure.

36. The method according to claim 32, further comprising: (d) releasing said compressed portion of said device.

37. The method of claim 36 further comprising: (e) repeating the following steps until the device is fully enveloped by said sleeve tip:

(1) compressing at least a portion of said device around said inner tube;
(2) advancing said retractable sleeve structure so that the sleeve tip extends longitudinally over at least a part of the uncompressed portion of said device; and
(3) releasing said compressed portion of said device.

38. The method according to claim 32, wherein said device is a stent or graft.

39. The method according to claim 32, further comprising:
(d) releasing the fluid from the sealed chamber.

* * * * *